United States Patent [19]

DiBella

[11] Patent Number: 4,469,644

[45] Date of Patent: Sep. 4, 1984

[54] PROCESS FOR THE PRODUCTION OF TRIARYL PHOSPHATES

[75] Inventor: Eugene P. DiBella, Piscataway, N.J.

[73] Assignee: Borg-Warner Chemicals, Inc., Parkersburg, W. Va.

[21] Appl. No.: 427,409

[22] Filed: Sep. 29, 1982

[51] Int. Cl.$^3$ .............................................. C07F 9/09
[52] U.S. Cl. .................................... 260/985; 260/966
[58] Field of Search ................................ 260/985, 966

[56] References Cited

U.S. PATENT DOCUMENTS 3,939,229  2/1976  Hechenbleikner et al. ........ 260/985
4,202,843  5/1980  DiBella ............................... 260/985

Primary Examiner—Anton H. Sutto
Attorney, Agent, or Firm—Richard J. Schlott

[57] ABSTRACT

Triaryl phosphates are prepared in good yields by contacting the corresponding triaryl phosphites with an oxygen-containing gas in the presence of a catalyst that comprises a halogen component and a cationic cocatalyst at a temperature in the range of 10° C. to 200° C.

The catalyst preferably comprises iodine and ferric chloride.

8 Claims, No Drawings

PROCESS FOR THE PRODUCTION OF TRIARYL PHOSPHATES

This invention relates to a process for the production of organic phosphates. More particularly, it relates to a process for the production of triaryl phosphates by the oxygenation of the corresponding triaryl phosphites in the presence of a catalyst that comprises a halogen component and a cationic cocatalyst.

A number of processes for the production of organic phosphates by the oxidation of organic phosphites have been reported. Processes that employ such oxidizing agents as hydrogen peroxide, peracids, epoxides, nitrogen oxides, sulfur trioxide, or ozone as the oxidizing agent have generally proven unsatisfactory for the commercial production of organic phosphates because they do not give high yields of the phosphates, because they produce substantial amounts of hydrolyzed phosphates and other undesirable reaction products, and because they require the use of costly reagents and processing procedures. A review of these and other processes for the oxidation of organic phosphites to phosphates appears in "Organic Phosphorus Compounds", Volume 6, by G. M. Kosolapoff and L. Maier (New York: John Wiley and Sons, 1973), page 247 ff.

Processes in which organic phosphites are oxidized with oxygen in the presence of catalysts have also been reported. Baranauckas et al. disclosed processes in which phosphites were oxidized by contacting them with oxygen in the presence of a catalyst that is copper, a transition metal, or an oxide of copper or a transition metal (U.S. Pat. No. 3,333,030) or a catalyst that is aluminum oxide or vanadium pentoxide (U.S. Pat. No. 3,136,805). Heckenbleikner et al. disclosed processes for the preparation of trialkyl and trialkenyl phosphates by oxidation of the corresponding phosphite with oxygen or an oxygen-containing gas in the presence of a catalyst that is a transition metal carboxylate (U.S. Pat. No. 3,939,229) or in the presence of a source of free radicals, e.g., an organic peroxide or an azo compound, and in the presence of a light of wavelength of 2000 to 4000 Å (U.S. Pat. No. 3,923,620). A process in which organic phosphites are oxidized using oxygen and a peroxide catalyst was disclosed by Nehmsmann et al. in U.S. Pat. No. 3,277,217. While these processes give good results when trialkyl or trialkenyl phosphites are the starting materials, they usually require lengthy reaction periods for the conversion of triaryl phosphites to triaryl phosphates. In addition, they may require high temperatures and precise control of reaction conditions if satisfactory yields are to be obtained, they may require the use of costly reactants, and they form products that contain catalyst and other impurities that must be removed before the products can be used, for example, as plasticizers, lubricant additives, or flame-retardants. In U.S. Pat. No. 4,202,844, DiBella disclosed a process in which triaryl phosphates are produced by the nitrogen dioxide-catalyzed oxygenation of the corresponding phosphites.

In accordance with this invention, it has been found that triaryl phosphates can be prepared in high yields by the oxygenation of the corresponding triaryl phosphites in the presence of a catalyst that comprises a halogen component and a cationic cocatalyst. This process provides an efficient low-cost procedure for the production of triaryl phosphates that are used commercially, for example, as plasticizers, lubricant additives or flame-retardants. In addition, the high activity of the preferred catalyst system allows considerable flexibility in the choice of reaction conditions, thus providing the advantage of process latitude in a commercial operation.

In the process of this invention, a triaryl phosphite is contacted with an oxygen-containing gas, which is preferably oxygen, in the presence of a catalyst that comprises a halogen component and a cationic cocatalyst at a temperature in the range of 10° C. to 200° C., preferably in the range of 35° C. to 140° C. Particularly good results have been obtained when the oxidation was carried out at a temperature in the range of 50° C. to 100° C.

The addition of the oxygen-containing gas to the phosphite in continued until sufficient oxygen has been added for the quantitative conversion of the phosphite to phosphate. The oxygenation is preferably carried out in an autoclave or other closed system in which sufficient oxygen or oxygen-containing gas is added to maintain a pressure in the range of 1 atmosphere to 10 atmospheres at a rate that is substantially equivalent to that at which it is being consumed by the reaction. The reaction can also be carried out by sparging the reaction mixture with the oxygen-containing gas under atmospheric or subatmospheric pressure. An excess of oxygen may be present during the oxidation reaction. In most cases, the amount of oxygen that is added to the phosphite is from 100% to 3000% of the stoichiometric amount required for the oxidation, with most favorable results being obtained when from 100% to 200% of the stoichiometric amount of oxygen is used.

The catalysts that are used in the process of this invention comprise a halogen component that may be iodine, bromine, or a mixture thereof and a cationic cocatalyst. The halogen component is preferably iodine. The useful cationic cocatalysts are metal species that are capable of effecting oxidation of the iodide portion of the intermediate P-I linkage that is formed when the triaryl phosphite is contacted with iodine and that will undergo rapid reoxidation to the original higher oxidation state when contacted with molecular oxygen. Among the useful cocatalysts are compounds of iron, cerium, copper, manganese, mercury, thallium, gold, silver, thorium, cobalt, and nickel, and mixtures thereof. The metals in these compounds may be either in their highest oxidation states or in lower oxidation states which are converted to the active higher states under the reaction conditions. The most effective of the cocatalysts are compounds of iron (III), cerium (IV), copper (II), and manganese (III). The oxidizing cations are preferably added to the reaction mixture in the form of soluble compounds, for example, acetates, chlorides, or 2,4-pentanedionates, in order to maximize the oxidation rate. The preferred cationic cocatalyst is ferric chloride.

The amount of the catalyst used is that which will provide from 0.01 to 100 mole percent of the halogen component and from 0.01 to 100 mole percent of the cationic cocatalyst based on the triaryl phosphite reactant. The catalyst preferably contains from 0.2 to 3 mole percent of the halogen component based on the triaryl phosphite reactant. When the cationic cocatalyst is present as a metal compound that is soluble in the reaction mixture, 0.2 to 10 mole percent of the cocatalyst is preferably used. When the catalyst comprises iodine and ferric chloride, it preferably contains 0.2 to 3 mole percent of iodine and 0.2 to 3 mole percent of ferric chloride based on the phosphite reactant. Higher levels, that is, 5 mole percent or more of the cationic cocatalyst, are preferably used when the cocatalyst is a compound, for example, a metal oxide, that is insoluble in the reaction mixture.

The oxidation of the phosphites may be carried out in a solvent medium, but the use of a solvent medium is not essential. The solvents that can be used are inexpensive volatile liquids that are resistant to oxidation, for example, aromatic hydrocarbons and halogenated aliphatic hydrocarbons.

During the catalyzed oxygenation of the phosphites, the reaction mixture should be agitated efficiently to insure adequate contact between the phosphite and the oxygen-containing gas.

When the oxidation of the triaryl phosphite has been completed, the reaction mixture may be heated under subatmospheric pressure to separae the solvent and residual gases from the product. The triaryl phosphate may be further purified, for example, by filtration, washing, distillation, and/or crystallization.

The organic phosphites that can be converted to the corresponding phosphae by the process of this invention are triaryl phosphites that have the structural formula

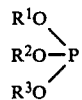

wherein $R^1$, $R^2$, and $R^3$ each represents phenyl, alkylphenyl, halophenyl, or nitrophenyl. Illustrative of these phosphites are the following: triphenyl phosphite, tricresyl phosphite, trixylyl phosphite, tri(isopropylphenyl) phosphite, tri(tert. butylphenyl) phosphite, tri(p-chlorophenyl) phosphite, tri(m-nitrophenyl) phosphite, phenyl di(isopropylphenyl) phosphite, diphenyl isopropylphenyl phosphite, cresyl di(2,4-dibromophenyl) phosphite, cresyl di(2,3,6-trichlorophenyl) phosphite, cresyl di(2-tetradecylphenyl) phosphite, 3-nitrophenyl di(p-chlorophenyl) phosphite, p-octylphenyl di(dinitrophenyl) phosphite, di(2,3-diethylphenyl) hexylphenyl phosphite, and mixtures thereof.

When alkyl phosphites are oxygenated in the presence of the catalysts of this invention, competitive side reactions take place, and there is only a low conversion of the alkyl phosphite to alkyl phosphate.

The invention is further illustrated by the examples that follow.

EXAMPLE 1

To a one-liter, stainless steel Parr autoclave vessel equipped for agitation, heating/cooling, and gas pressurization were charged 710 grams (2.29 moles) of triphenyl phosphite, 1.78 grams (0.0070 mole; 0.31 mole %) of iodine, and 2.34 grams (0.0144 mole; 0.63 mole %) of anhydrous iron (III) chloride. The mixture was heated to 115°–120° C. with efficient agitation and pressurized with oxygen at 55 psig. These conditions were maintained by applying sufficient cooling to control the accompanying exotherm which subsided after about 2.5 hours. The oxygenation was continued until no oxygen pressure drop was observed when the reaction vessel was isolated from the outside pressure line. The total reaction time was 5 hours. When the reaction vessel was vented, there was obtained 747 grams of triphenyl phosphate, an amber liquid that solidified upon cooling to room temperature. Gas chromatography showed the absence of triphenyl phosphite, thus demonstrating that the conversion of the phosphite to the phosphate was quantitative.

This crude product can be further processed by conventional techniques to remove the catalyst components from it. For example, both catalyst components can be removed by washing the crude product with aqueous sodium bisulfite solution or dilute hypophosphorus acid. A subsequent wash with dilute sodium carbonate or sodium hydroxide solution will insure the removal of traces of iron or iodide ions as well as residual acidity prior to a distillation step, which will improve the color of the product.

EXAMPLE 2

A series of iodine/iron (III) chloride-catalyzed oxygenations of triphenyl phosphite under various reaction conditions was carried out by the procedure described in Example 1. The reaction conditions employed and the results obtained are set forth in Table I. Except where otherwise indicated, the oxidations were carried out using 0.25–0.50 mole of triphenyl phosphite in a Fischer-Porter pressure apparatus fitted with a 6 oz. glass bottle and set up for magnetic stirrer agitation.

TABLE I

OXYGENATION OF TRIPHENYL PHOSPHITE USING $I_2$/$FeCl_3$ CATALYSIS UNDER VARIOUS CONDITIONS

| Exp. No. | Catalyst Level (Mole %) Iodine | Catalyst Level (Mole %) Ferric Chloride | Oxygen Pressure (psig) | Temp. (°C.) | Time (Hrs.) | Molar Conversion to Phosphate (%) | Notes |
|---|---|---|---|---|---|---|---|
| 2A | 0.25 | 6.5 | 100 | 90–100 | 8 | 100 | |
| 2B | 0.31 | 0.27 | 55 | 115–120 | 4 | 100 | (1) |
| 2C | 0.31 | 0.48 | 0 | 95–100 | 5 | 82 | (2) |
| 2D | 0.31 | 0.48 | 52 | 115–120 | 7 | 100 | |
| 2E | 0.31 | 0.62 | 55 | 115–120 | 4.5 | 100 | (1) |
| 2F | 0.31 | 0.72 | 53 | 115–120 | 6.5 | 100 | |
| 2G | 0.31 | 1.91 | 55 | 95–100 | 5 | 100 | |
| 2H | 0.39 | 0.64 | 55 | 135–140 | 4.5 | 99 | |
| 2I | 0.80 | 1.20 | 50 | 90–95 | 0.75 | 100 | |
| 2J | 1.60 | 2.50 | 100 | 55–60 | 0.5 | 100 | |
| 2K | 2.40 | 0.68 | 50 | 80–85 | 0.75 | 100 | |
| 2L | 2.40 | 1.40 | 100 | 55–60 | 0.75 | 100 | |
| 2M | 2.40 | 5.00 | 100 | 35–40 | 3 | 100 | |

(1) Carried out using 2.3 moles of triphenyl phosphite in a stainless steel autoclave reactor.
(2) Carried out using 1.3 mole of triphenyl phosphite in a stirred glass autoclave using subsurface sparging with oxygen at the rate of 0.40 mole $O_2$/mole phosphite under atmospheric pressure. Corresponds to a 2.9-fold excess of oxygen.

From the data in Table I, the following conclusions can be drawn with respect to the iodine/iron (III) chloride-catalyzed system:

1. Operation under superatmospheric pressure favors complete reaction.
2. Higher catalyst levels allow operation at lower temperatures.
3. Iodine appears to be the more important catalyst component with respect to reaction rate. Compare Examples 2A–2H with Examples 2I–2M.

EXAMPLE 3

A. To a Fischer-Porter pressure apparatus fitted with a 6 oz. glass bottle and set-up for magnetic stirrer agitation, were charged 77.5 grams (0.25 mole) of triphenyl phosphite, 1.0 gram (0.0079 mole; 1.57 mole %) of iodine, and 1.0 gram (0.0028 mole; 1.12 mole %) of iron (III) 2,4-pentanedionate. The mixture was oxygenated at 80 psig oxygen pressure at 55°–60° C. Oxygen absorption ceased after about 1.5 hours. After maintaining these conditons for another 0.5 hour, the system was vented. The resulting reaction mixture, which solidified on cooling, weighed 83.8 grams. Gas chromatography indicated quantitative conversion of the triphenyl phosphite to triphenyl phosphate.

B. For comparative purposes, the procedure described in Example 3A was repeated using iodine but without the iron (III) 2,4-pentanedionate. No oxygen uptake occurred in 4 hours.

C. For comparative purposes, the procedure described in Example 3A was repeated using iron (III) 2,4-pentanedionate but without the iodine. No oxygen uptake occurred in 4 hours.

EXAMPLE 4

Using the Fischer-Porter pressure apparatus described in Example 3A, a mixture of 77.5 grams (0.25 mole) of triphenyl phosphite, 1.0 gram (0.0079 mole; 1.57 mole %) of iodine, and 1.0 gram (0.0125 mole Fe; 5.0 mole %) of iron (III) oxide was oxygenated at 100 psig oxygen pressure at 95°–100° C. for 6 hours. The reaction product, which weighed 82.3 grams, was shown by gas chromatography to contain 62% of triphenyl phosphate and 38% of unreacted triphenyl phosphite.

In this run, the iron (III) component of the catalyst was insoluble in the reaction mixture. The availability (concentration) of iron (III) ions required for the catalytic oxygenation was thus limited and conversion to the phosphate was incomplete.

EXAMPLE 5

A. An iron (III) polyphosphate composition was prepared by vigorously agitating a mixture of 95.3 grams of iron (III) orthophosphate dihydrate, 300 grams of water, and 47 grams of 37% hydrochloric acid in a Waring Blendor at room temperature for 5 minutes. The resulting solid product was collected and dried in a furnace at 400° C. There was obtained 81.3 grams of an iron (III) polyphosphate composition that contained 34.2% of iron and 22.7% of phosphorus.

B. Using a Fischer-Porter pressure apparatus with a 12 oz. bottle, a mixture of 400 grams (1.29 moles) of triphenyl phosphite, 3.0 grams (0.012 mole; 0.92 mole %) of iodine, and 16.2 grams (0.099 mole Fe; 7.67 mole %) of the iron (III) polyphosphate composition was oxygenated at 100 psig oxygen pressure at 135°–140° C. for 26 hours. The reaction product, which weighed 425.6 grams, contained the iron polyphosphate cocatalyst as an insoluble solid phase. Analysis of the liquid phase by gas chromatography showed a 76% conversion to the phosphate. The balance of the liquid phase was unconverted triphenyl phosphite.

Here, as in Example 4, the insolubility of the iron (III) cocatalyst was primarily responsible for the incomplete conversion of the phosphite to phosphate.

EXAMPLE 6

A series of oxygenations of triphenyl phosphite was carried out in a Fischer-Porter exposure apparatus by the procedure described in the previous examples using as catalyst metal compounds other than iron (III) compounds in combination with iodine. The reaction conditions employed and the results obtained are set forth in Table II.

The reaction mixtures that contained the 2,4-pentanedionates of cerium, copper, or manganese were homogeneous. Cerium oxide and thorium oxide were not soluble in the reaction mixture.

TABLE II
OXYGENATION OF TRIPHENYL PHOSPHITE USING VARIOUS COCATALYSTS IN COMBINATION WITH IODINE

| Exp. No. | Cationic Cocatalyst | Catalyst System Level (Mole %) Iodine | Catalyst System Level (Mole %) Metal | Oxygen Pressure (psig) | Temp. (°C.) | Time (Hrs) | Molar Conversion to Phosphate (%) |
|---|---|---|---|---|---|---|---|
| 6A | Cerium (III) 2,4-pentanedionate | 1.6 | 1.7 | 100 | 95–100 | 6 | 26 |
| 6B | Cerium (IV) Oxide | 1.6 | 2.3 | 100 | 120–125 | 2 | 22 |
| 6C | Copper (II) 2,4-pentanedionate | 1.6 | 2.5 | 100 | 95–100 | 5 | 27 |
| 6D | Manganese (II) 2,4-pentanedionate | 1.6 | 2.6 | 100 | 95–100 | 16 | 28 |
| 6E | Thorium (IV) oxide | 1.6 | 1.5 | 100 | 120–125 | 6 | 99 |

EXAMPLE 7

The procedure described in Example 3 was repeated using a bromine/cerium (III) 2,4-pentanedionate catalyst that contained 7.00 mole % of bromine and 1.60 mole % of cerium (III), based on the triphenyl phosphite. The reaction mixture was oxygenated at 100 psig oxygen pressure at 95°–100° C. for 4 hours. The conversion of triphenyl phosphite to triphenyl phosphate was 98%.

EXAMPLE 8

A. To a mixture of 3005 grams (32 moles) of phenol, 60 grams of acid clay (Filtrol-13) and 6 grams of p-toluene-sulfonic acid was added 625 grams (14.9 moles) of propylene over a period of 8 hours during which the reaction mixture was efficiently stirred and maintained at 130°–135° C. Following a post-heating period of 3 hours at 180° C. to effect disproportionation/isomerization to a composition low in ortho substitution, the reaction mixture was cooled to 90° C. and filtered.

There was obtained 3570 grams of an isopropylphenol/phenol product (98.4% yield) having the following composition: phenol, 49.9%; o-isopropylphenol, 20.6%; m- and p-isopropylphenols, 21.9%; 2,6-diisopropylphenol, 0.9%; other diisopropylphenols, 6.6%; and 2,4,6-triisopropylphenol, 0.1%.

To this isopropylphenol/phenol mixture was added 1375 grams (10 moles) of phosphorus trichloride over a period of 6 hours while the reaction mixture was efficiently stirred and maintained at 60°–65° C. and hydrogen chloride was evolved steadily. After the reaction mixture had been heated at 220° C. for 2 hours to complete the removal of 1116 grams of hydrogen chloride and other volatile compounds from it, it was cooled to 170° C. and vacuum was applied gradually to remove the last traces of hydrogen chloride. The reaction was then heated at 170°–175° C./1 mm to distill 289 grams of phenolic compounds from it. The residue was cooled to 90°–95° C., stirred with a mixture of 20 grams of sodium carbonate, 20 grams of clay acid (Attasorb LVM), and 20 grams of filter-aid (Celite 535) at this temperature for 1 hour, and filtered.

There was obtained in 94% yield an isopropylphenyl/phenyl phosphite composition that had an acid number of 0.01, specific gravity at 25° C. of 1.117, and viscosity at 25° C. of 37.6 centistokes and that contained 50 ppm of labile chlorine.

B. Using the procedure described in Example 1, 426.2 grams (1.16 mole) of the isopropylphenyl/phenyl phosphite composition was oxygenated in the presence of a catalyst system that contained 1.06 gram (0.0042 mole; 0.34 mole %) of iodine and 1.39 gram (0.0086 mole; 0.74 mole %) of iron (III) chloride. The reaction was carried out at an oxygen pressure of 55 psig at 110°–115° C. for 5.5 hours. The crude reaction product, which weighed 448.6 grams, was shown by infrared analysis to consist entirely of triaryl phosphate components. The oxygenation reaction was thus quantitative.

EXAMPLE 9

Using a Fischer-Porter pressure apparatus with a 6 oz. bottle, a mixture of 100 grams (0.272 mole) of the isopropylphenyl/phenyl phosphite composition of Example 8A, 10.0 grams (0.0394 mole; 14.5 mole %) of iodine, and 6.0 grams (0.037 mole Fe; 13.7 mole %) of the iron (III) polyphosphite composition of Example 5A was oxygenated at 100 psig at 95°–100° C. for 8 hours. The reaction product, which weighed 120.7 grams, was shown by infrared analysis to consist entirely of a isopropylphenyl/phenyl phosphate composition.

EXAMPLE 10

A. To a mixture of 540 grams (3.80 moles) of tert.butylphenyl, 430 grams (4.57 moles) of phenol and 520 grams of toluene was added with efficient agitation 365 grams (2.65 moles) of phosphorus trichloride over a period of 3 hours under ambient conditions. The ensuing reaction was endothermic and was accompanied by the evolution of hydrogen chloride. The reaction mixture was heated to 110° C. to remove residual hydrogen chloride. The toluene was then removed by overhead distillation to a pot temperature of 140° C. after which vacuum was gradually applied and the reaction mixture heated to a pot temperature of 200° C. at 1 mm absolute pressure in order to distill off free phenolic compounds. The resulting tert.butylphenyl/phenyl phosphite composition weighed 757 grams and had an acid no. of 1.4 and a phosphorus content of 7.64%. The yield of phosphite was 71%.

B. Using the procedure described in Example 1, a reaction mixture that contained 668 grams (1.70 mole) of the tert.butylphenyl/phenyl phosphite composition of Example 10A, 1.72 grams (0.0068 mole; 0.40 mole %) of iodine, and 2.42 grams (0.0150 mole; 0.88 mole %) of anhydrous iron (III) chloride was oxygenated at 55 psig at 115°–120° C. for 6 hours. The reaction product, which weighed 722 grams, was shown by infrared analysis to consist entirely of tert.butylphenyl/phenyl phosphates. Gas chromatography indicated that the product contained 8.3% of triphenyl phosphate, 31.4% of diphenyl tert.butylphenyl phosphate, 41.3% of phenyl di-tert.butylphenyl phosphate, and 19.0% of tri-tert.butylphenylphosphate.

When this product was purified by methods known in the art, material meeting commercial plasticizer specifications was obtained.

Each of the other triaryl phosphites disclosed herein may be oxygenated in a similar manner to the corresponding triaryl phosphate.

What is claimed is:

1. The process for the production of triaryl phosphates that comprises contacting a triaryl phosphite having the structural formula

wherein $R^1$, $R^2$, and $R^3$ each represent phenyl, alkylphenyl, halophenyl, or nitrophenyl with an oxygen-containing gas in the presence of a catalyst that comprises in combination (1) iodine or bromine, and (2) an oxide or soluble salt of iron, cerium, copper, manganese or thorium at a temperature in the range of 10° C. to 200° C.

2. The process of claim 1 wherein said metal is in its highest oxidation state or in a lower oxidation state that is converted to the highest state under the reaction conditions.

3. The process of claim 1 wherein the halogen component of the catalyst comprises iodine.

4. The process of claim 1 wherein the catalyst comprises iodine and ferric chloride.

5. The process of claim 1 wherein the amount of catalyst used is that which will provide 0.01 to 100 mole percent of said halogen component and 0.01 to 100 mole percent of said cationic cocatalyst, based on the triaryl phosphite reactant.

6. The process of claim 1 wherein the amount of catalyst used is that which will provide 0.2 to 3 mole percent of iodine and 0.2 to 3 mole percent of ferric chloride, based on the triaryl phosphite reactant.

7. The process of claim 1 wherein the triaryl phosphite is triphenyl phosphite.

8. The process of claim 1 wherein the triaryl phosphite is isopropylphenyl/phenyl phosphite.

* * * * *